US007144409B2

(12) United States Patent
Aranyi

(10) Patent No.: US 7,144,409 B2
(45) Date of Patent: Dec. 5, 2006

(54) SURGICAL GRASPING INSTRUMENT

(75) Inventor: Ernest Aranyi, Easton, CT (US)

(73) Assignee: Tyco Healthcare Group LP, North Haven, CT (US)

( * ) Notice: Subject to any disclaimer, the term of this patent is extended or adjusted under 35 U.S.C. 154(b) by 53 days.

(21) Appl. No.: 10/469,774

(22) PCT Filed: Mar. 5, 2002

(86) PCT No.: PCT/US02/06438

§ 371 (c)(1),
(2), (4) Date: Sep. 4, 2003

(87) PCT Pub. No.: WO02/069814

PCT Pub. Date: Sep. 12, 2002

(65) Prior Publication Data

US 2004/0084497 A1    May 6, 2004

Related U.S. Application Data

(60) Provisional application No. 60/273,522, filed on Mar. 5, 2001.

(51) Int. Cl.
*A61B 17/00* (2006.01)
(52) U.S. Cl. .................................................. 606/207
(58) Field of Classification Search ........ 606/205–210, 606/151, 157, 152, 139, 142, 144
See application file for complete search history.

(56) References Cited

U.S. PATENT DOCUMENTS

| 4,605,002 | A | * | 8/1986 | Rebuffat | 606/207 |
|---|---|---|---|---|---|
| 4,803,983 | A | * | 2/1989 | Siegel | 606/207 |
| 5,354,312 | A | * | 10/1994 | Brinkerhoff et al. | 606/207 |
| 5,443,479 | A | | 8/1995 | Bressi, Jr. | |
| 5,626,609 | A | | 5/1997 | Zvenyatsky et al. | |
| 5,797,958 | A | | 8/1998 | Yoon | |
| 6,086,606 | A | | 7/2000 | Knodel et al. | |

FOREIGN PATENT DOCUMENTS

EP    0 588 658    3/1994

* cited by examiner

*Primary Examiner*—Kevin T. Truong

(57) ABSTRACT

A surgical grasping instrument for grasping an elongated implement, which comprises a frame; an elongated member connected to the frame and extending distally therefrom, the elongated member defining a longitudinal axis; and a pair of jaw members operatively connected to the elongated member, the jaw members being adapted for movement between an open position and a closed position, at least one of the jaw members having a recess defined therein and arranged about a central recess axis extending at an angle of about 35° or less relative to the longitudinal axis of the elongated member, wherein upon movement of the jaw members to the closed position, the jaw members form a holding groove that can engage and firmly secure the elongated implement.

19 Claims, 5 Drawing Sheets

SURGICAL GRASPING INSTRUMENT

CROSS REFERENCE TO RELATED APPLICATION

The present application claims priority of U.S. provisional application Ser. No. 60/273,522 filed Mar. 5, 2001, the entire contents of which is hereby incorporated by reference.

BACKGROUND

1. Technical Field

The present invention relates to surgical instruments, and more particularly, to an endoscopic grasping instrument having jaw members advantageously designed to engage and firmly secure a surgical implement at a desired orientation to facilitate manipulation of the implement about the surgical site, and/or mounting of the instrument to other surgical devices, for example, to a surgical stapler.

2. Background of Related Art

Circular anastomosis is the surgical joining of separate hollow body organ sections so that the sections intercommunicate. Typically, the anastomosis procedure follows surgery in which a diseased or defective section of hollow tissue is removed and the remaining end sections are to be joined. In accordance with such procedures, the operative tissue is exposed by making at least one extensive tissue incision, in the body cavity wall and folding the cut tissue back to provide access to the surgical site. The diseased section of the organ is removed thereby leaving two separate end sections of organ to be thereafter fastened by anastomosis by means of a stapling instrument. The stapling instrument drives a circular array of staples through the end sections and simultaneously cores out any overlapping tissue to free the tubular passages.

Examples of such instruments for performing anastomosis of hollow organs are described in U.S. Pat. Nos. 4,304,236, 4,379,457, 4,573,468, 4,576,167, 4,603,693 and 4,646,745, the entirety of each of which is incorporated herein by reference. In instruments of the types exemplified by these patents, opposed end portions of the organs to be stapled are clamped between an anvil component and a staple holding component (i.e., staple cartridge), both of which are located at the distal end of the anastomosis instrument. The clamped tissue is stapled by driving one or more staples from the staple cartridge so that the ends of the staples pass through the tissue and are clinched by the anvil component.

In a typical application of joining first and second intestinal sections together, the intestinal section in question is removed leaving the first and second intestinal end sections to be joined by anastomosis. The stapling instrument, having the anvil component operatively coupled thereto, is applied to the operative site. Each end of the intestinal sections to be attached is then secured to their respective stapler cartridge and anvil assembly by a well-known purse string stitch to cause the tissue portions to tighten and to remain on the apparatus in position for permanent attachment by the staples. Thereafter, the anvil component is manually brought into close proximity to the staple cartridge. The instrument is fired and the intestinal sections are attached by circular rows of staples or fasteners.

In some applications of the circular anastomosis technique, it is necessary to utilize a surgical instrument in which the anvil component, typically an anvil assembly comprised of an anvil head and a shaft, is detachably mounted to the staple cartridge. In such cases, the stapling instrument is introduced either surgically or transanally into the first intestinal section without the anvil assembly in place. The anvil assembly is subsequently surgically inserted within the second intestinal section. Both intestinal sections are then secured respectively to the anvil assembly and stapler cartridge by a drawstring type suture. It is then necessary to grasp and hold the shaft of the anvil assembly in order to properly mount the anvil assembly or component onto or within the cartridge assembly portion of the instrument. The instrument is then fired to complete the anastomosis.

However, the task of grasping the anvil and mounting it to the anastomosis instrument has proven to be quite difficult, particularly in restricted operative sites which are surrounded by close organs, tissue, etc. Conventional means incorporate the use of a conventional forceps or similar device. However known forceps typically include flat forceps jaw surfaces which are not suitable for grasping a round implant such as an anvil or anvil shaft. Also, the grasper jaws typically are disposed along the longitudinal axis of the forceps. Such a configuration often requires ample space in the abdominal cavity to grasp and manipulate the instrument. Further, the presence of body fluids, blood, etc. also complicate the procedure.

Accordingly, the present disclosure is directed to an endoscopic surgical instrument having jaws which are adapted to provide a secure grip of the shaft of or for an anvil together with enhanced freedom of movement of the surgical instrument within the patients' body without slippage and/or interference with body organs or tissue of the patient, or other obstructions. Further, the surgical jaws are suitably disposed to provide improved holding of a cylindrical or rod-like object at a desired orientation in which the longitudinal central axis of the cylindrical or rod-like object is substantially parallel or slightly oblique with respect to the longitudinal central axis of the elongated shaft of the surgical instrument. Such a configuration requires less space in the abdominal cavity to grasp and manipulate the instrument. Yet further, the anvil shaft is suitably designed to facilitate mounting of the shaft to the anastomosis instrument.

SUMMARY

The surgical jaws according to the present invention are adapted for use with an endoscopic surgical instrument and are advantageously configured to facilitate grasping of a shaft of or for an anvil assembly of a circular surgical stapling device and manipulation of the anvil assembly about the operative site. Generally, the present invention is directed to a surgical instrument including a frame or handle member and an elongated shaft member that has a longitudinal axis, and is operatively coupled to the frame or handle member.

In a preferred embodiment, a pair of jaw members are operatively connected to the elongated member, and are adapted for movement between an open position and a closed position. At least one of the pair of jaw members includes a facing surface having a recess therein and arranged about a central recess axis extending at an angle of about 35° or less relative to the longitudinal axis of the elongated member. In use, upon movement of the jaw members to the closed position, the jaw members form a holding groove that engages and firmly secures an elongated implement therein. Each of the jaw members can have a recess formed therein.

Preferably, the central recess axis is about 25° relative to the longitudinal axis of the elongated member.

In a further preferred embodiment each jaw member includes a distal gripper portion wherein at least one distal gripper portion of the pair has the recess therethrough. Each distal gripper portion extends along an axis ranging from about 55° to about 75° relative to the longitudinal axis of the elongated member. Preferably, the axis of each gripper portion is about 65° relative to the longitudinal axis.

In an alternative preferred embodiment, according to the present invention, the endoscopic surgical instrument includes a frame member and an elongate shaft, wherein the elongate shaft has a proximal end operatively coupled to the frame member and a distal end. The elongate shaft defines a longitudinal axis. The endoscopic surgical instrument further includes an actuation mechanism coupled to the frame and jaw members, and includes a pair of jaw members operatively coupled to the distal end of the elongate shaft, the pair of jaw members being adapted to move between an open and a closed position. Each of the pair of jaw members includes a jaw axis and includes a distal gripper portion having a recess therein. The recesses are juxtaposed relative to one another for grasping a shaft of or for an anvil therein. As such, when the jaw members are in the closed position, the recesses define a holding groove having an axis that is oriented at an angle which is about 35° or less relative to the jaw axis.

Preferably, the axis of the holding groove is oriented at an angle which is between about 15° to about 35° relative to the jaw axis. More preferably, the axis of the holding groove is oriented at an angle which is about 25° relative to the jaw axis. The axis of the holding groove can be parallel to the jaw axis.

In a further embodiment, each jaw member of the endoscopic surgical instrument includes a base portion adapted to engage the distal end of the elongated shaft and a distal end portion having a longitudinal axis and that is located between the gripper portion and the base portion. The axis of the holding groove is oriented at an angle which is about 35° or less relative to the longitudinal axis of the distal end portion. Preferably, the axis of the holding groove is oriented at an angle which is about 25° relative to the jaw axis. The axis of the holding groove can be parallel to the jaw axis.

In yet another embodiment, each jaw member includes a base portion that has a diametric hole therethrough and about which the pair of jaws pivot and wherein each base portion includes a cam slot formed proximally of the diametric holes, wherein the cam slots cooperate with one another to transform an axial movement of the actuation means into the opening and closing of the pair of jaw members.

In still a further embodiment, each jaw member includes a base portion and an adjacent intermediate body portion that includes a distal end portion which is parallel to the jaw axis and which is spaced a distance transversely from an axis defined by each base portion.

BRIEF DESCRIPTION OF THE DRAWINGS

The accompanying drawings, which are incorporated in and constitute a part of this specification, illustrate embodiments of the invention and, together with a general description of the invention given above, and the detailed description of the embodiments given below, serve to explain the principles of the invention.

DETAILED DESCRIPTION OF PREFERRED EMBODIMENTS

Figure 1:
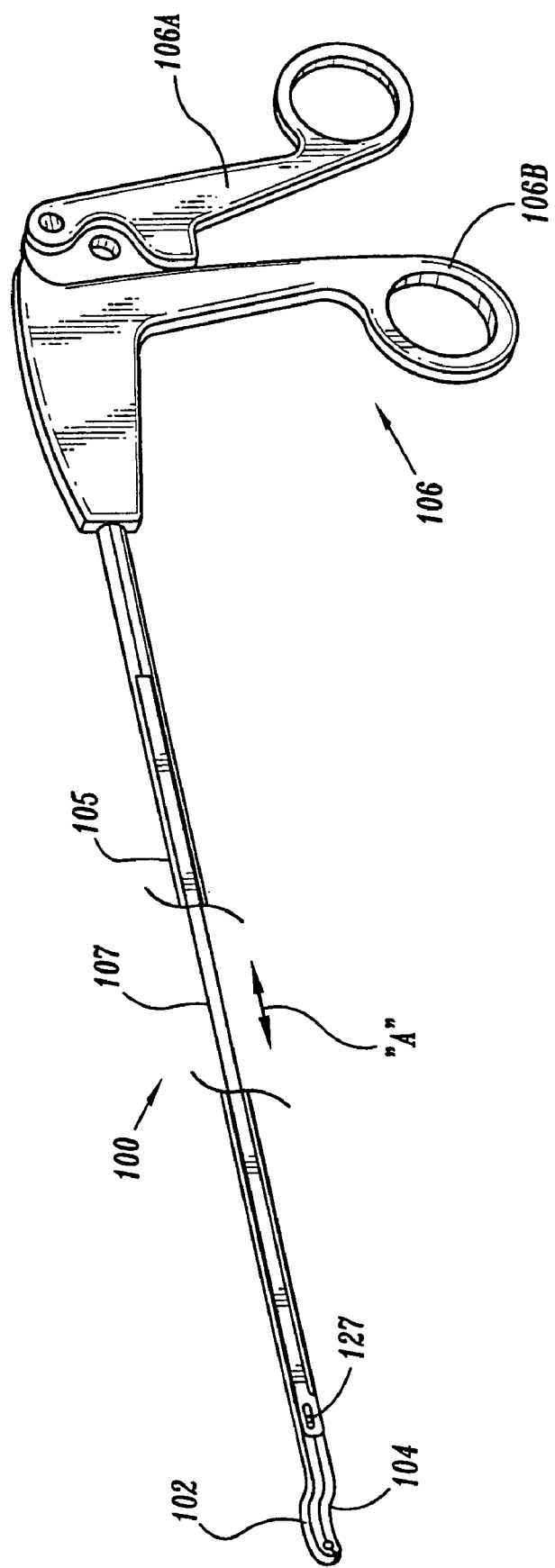
FIG. 1 is a perspective view of an endoscopic surgical instrument, in accordance with the present invention.

Preferred embodiments of the presently disclosed surgical jaws for an endoscopic surgical instrument will now be described in detail with reference to the drawing figures wherein like reference numerals identify similar or identical elements. As used herein, the term "distal" refers to that portion which is further from the user, while the term "proximal" refers to that portion which is closer to the user.

While the description below will relate to general anastomotic procedures, the present invention can be used in gastric bypass procedures disclosed in commonly assigned International Application Serial No. PCT/US01/07105, Publication No. WO 01/66020, entitled "Apparatus and Method for Performing a Bypass Procedure in a Digestive System", filed on Mar. 5, 2001, the entire contents of which are herein incorporated by reference.

Referring now in detail to FIGS. 1–7, an endoscopic surgical instrument in accordance with the present invention is generally designated as reference numeral 100. Endoscopic instrument 100 includes a pair of surgical jaw members 102 and 104 operatively coupled to a distal end of an enlongate shaft 105 defining a longitudinal axis, which jaw members 102 and 104 move, here pivot, in response to the operation of controls on or remote from a frame, e.g., the opening and closing of a handle assembly 106. Handle assembly 106 includes a pivoting handle 106A and a stationary handle 106B. In use, upon movement of pivoting handle 106A, an actuation mechanism, here shown as an inner rod 107, reciprocates in the longitudinal direction indicated by arrow "A" within elongate shaft 105 to operate jaw members 102 and 104. Such arrangement is appreciated by one skilled in the art. It is envisioned that a proximal end of elongate shaft 105 and a proximal end of inner rod 107 (i.e., the actuation means) can be operatively removably coupled to the distal end of a robotic armature (not shown), wherein the surgical instrument is positioned and maneuvered via a computer control system (not shown) which is connected to the robotic armature.

Figure 2:
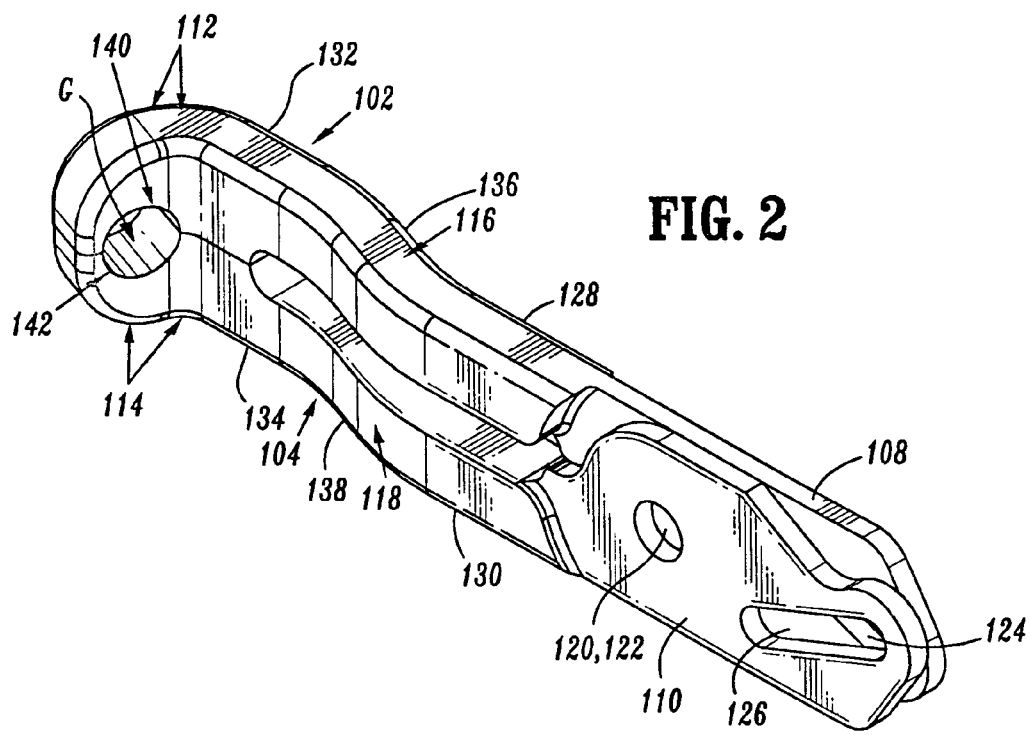
FIG. 2 is a perspective view of the jaw members of the surgical instrument.
Figure 3:
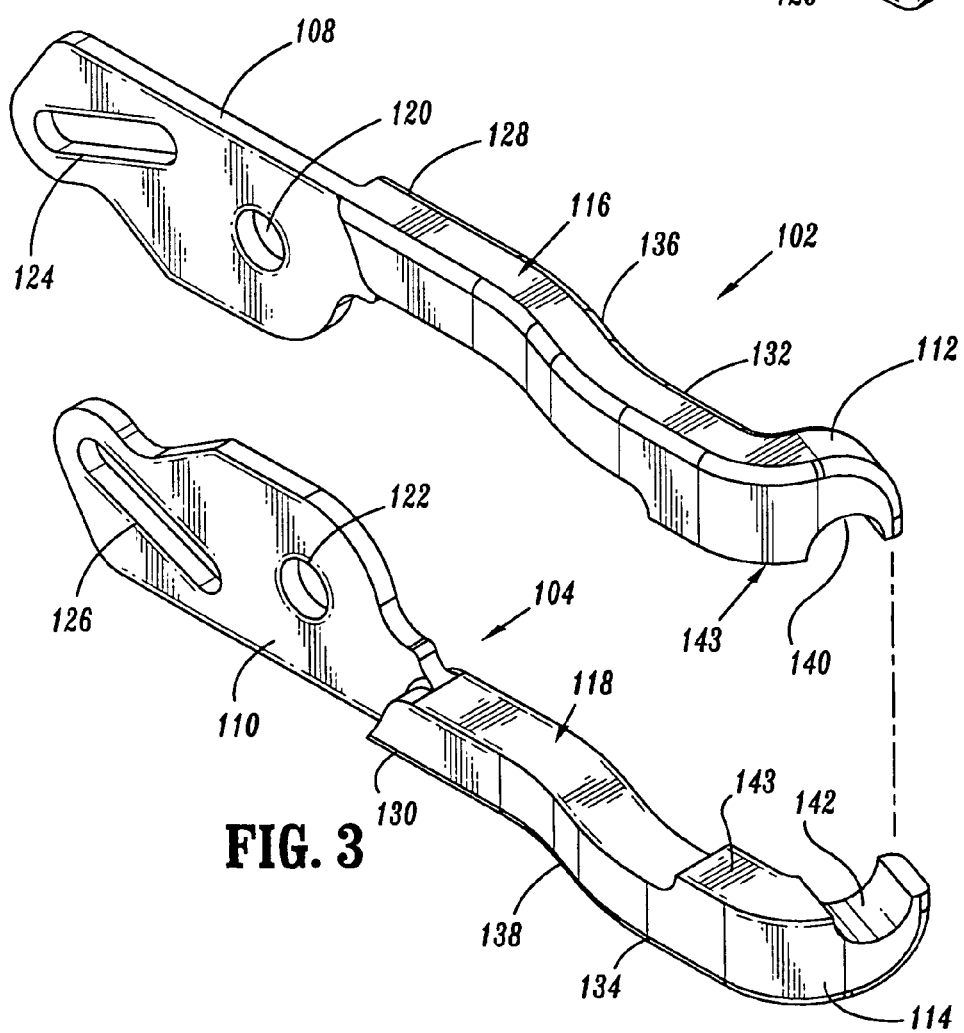
FIG. 3 is a perspective exploded view of the jaw members shown in FIG. 2.
Figure 4:
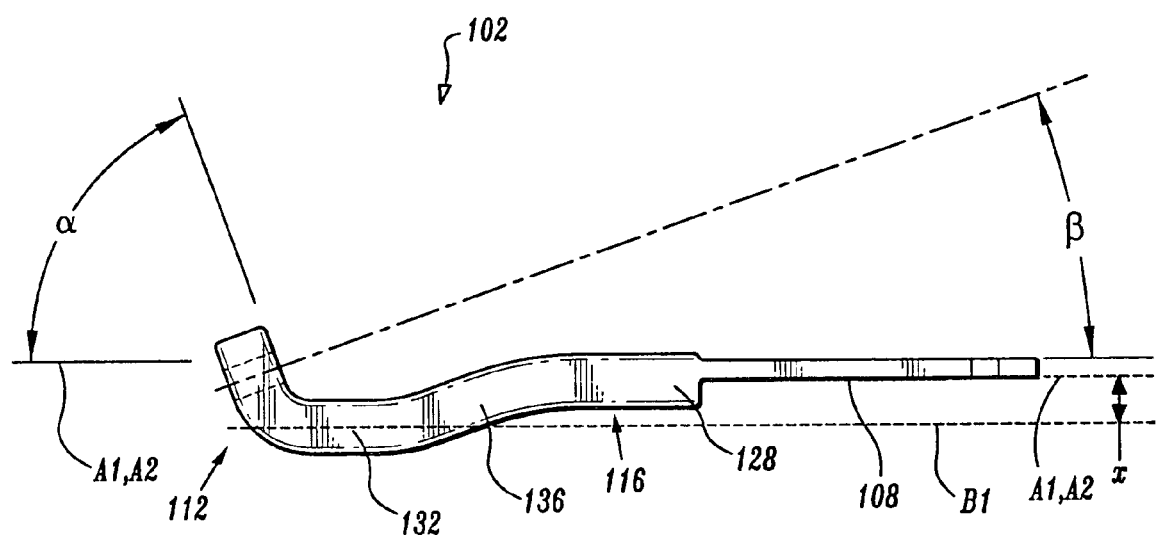
FIG. 4 is a side elevational view of a jaw member as shown in FIG. 2.

Referring now in detail to FIGS. 2–4, each jaw member 102 and 104 respectively includes a base portion 108 and 110 at their proximal end, a gripper portion 112 and 114 at their distal end, and an intermediate body portion 116 and 118 interconnecting base portion 108 and 110 to gripper portion 112 and 114, respectively.

Each base portion 108 and 110 includes a diametric radial hole 120 and 122, respectively for accepting a pivot pin (not shown) therethrough, which pivot pin is secured to surgical instrument 100. In operation, gripper portions 112 and 114 of jaw members 102 and 104, pivot about the pivot pin passing through radial holes 120 and 122 during an opening and a closing operation. Each base portion 108 and 110 is further provided with a cam slot 124 and 126, respectively, which slots are configured and adapted to receive a bearing post 127 (FIG. 1) therethrough. Preferably, cam slots 124 and 126 are formed proximally of radial holes 120 and 122, however, it is envisioned that cam slots 124 and 126 can be formed distally of radial holes 120 and 122.

Preferably, bearing post 127 is operatively coupled to handle assembly 106 via the inner rod 107. In use, as handle assembly 106 is actuated, the bearing post translates proximally and distally. Concomitantly, as handle assembly 106 is actuated, bearing post 127 slides within cam slots 124 and 126 in order to pivot gripper portions 112 and 114 about pivot pin, thereby opening and closing jaw members 102 and 104. In other words, when handle assembly 106 is actuated closed, the bearing post slides away from jaw members 102 and 104 within cam slots 124 and 126 thereby drawing jaw members 102 and 104 closed.

Each intermediate body portion 116 and 118 of jaw members 102 and 104 includes a proximal end portion 128 and 130 extending substantially axially and distally from base portion 108 and 110, respectively, wherein an axis "A1" of proximal end portions 128 and 130 is in the same plane as an axis "A2" of base portion 108 and 110 (see FIG. 4); and a distal end portion 132 and 134 extending substantially axially from an intermediate neck portion 136 and 138, respectively, wherein an axis "B1" of distal end portion 132 and 134 is in a plane spaced a distance "X" from axis "A1, A2" of base portion 108 and 100. Intermediate neck portion 136 and 138 interconnects proximal end portions 128 and 130 to distal end portions 132 and 134. The axis "A1, A2" is considered to be the axis of the jaw member, i.e., the jaw axis.

Gripper portions 112 and 114 extend distally from the ends of distal end portions 132 and 134 of jaw members 102 and 104. Each gripper portion 112 and 114 is provided with a recess 140, 142, preferably semi-cylindrical formed on corresponding facing surfaces 143. When such jaw members are in the closed position, recesses 140, 142 form a holding groove "G". Holding groove "G" extends through the entire thickness of each gripper portion 112 and 114. Preferably, recesses 140, 142, and holding groove "G" are formed to have a central axis which is orthogonal to the plane of gripper portions 112 and 114.

Preferably, gripper portions 112 and 114 are oriented at an angle "α" that is preferably from about 55° to about 75° relative to the longitudinal axis of elongated shaft 105, rod 107 or to axis "A1" of proximal end portions 128 and 130, axis "A2" of base portions 108 and 110 or axis "B1" of distal end portions 132 and 134. More preferably, angle "α" of the plane of gripper portions 112 and 114 is about 70° relative to axes "A1", "A2" or "B1". Most preferably, angle "α" of the plane of gripper portions 112 and 114 is about 65° relative to axes "A1", "A2" or "B1". Accordingly, the central axis of recesses 140, 142 and of holding groove "G" is at an angle "β" that is preferably from about 15° to about 35°, more preferably about 20° and most preferably about 25° relative to axes "A1", "A2" or "B1".

It is envisioned that each jaw member 102 and 104 can be provided with a gripper portion 112 and 114, at least one, preferably each, having one or more recesses 140 and/or 142, which recess or recesses form(s) a holding groove "G" when the jaw members are in the closed position. Preferably each recess and holding groove has a central axis that is about 35° or less relative to the longitudinal axis of elongate shaft 105, rod 107 or axis "A1", "A2" or "B1". Thus, the central axis of recesses 140, 142 and/or of holding groove "G" can be co-axial or co-planar with any one or more of such axes. In this manner, in use, when jaw members 102 and 104 grip a shaft, the axis of the shaft can be substantially co-planar with axes "A1", "A2" or "B1" thereby resulting in a substantially co-linear arrangement. In other words, the central axis of recesses 140, 142 and/or of holding groove "G" can be at an angle "β" which is 0° or parallel to the longitudinal axis of the elongate shaft.

Preferably, in use, when jaw members 102 and 104 are in a closed position, holding groove "G" is a substantially circular opening. While a substantially circular opening is preferred, especially for grasping a cylindrical portion of an anvil shaft, it is envisioned that the formed opening can take on any shape, including and not limited to, polygonal, rectangular, triangular, ovular, etc. Preferably, the inner surface of holding grooves 140 and 142 are smooth, however, it is envisioned that the inner surface of holding grooves 140 and 142 can be provided with a textured surface, including but not limited to, knurled, toothed, serrated, etc. The inner surface is designed to allow it to grasp the intended portion, e.g., one or more recesses of or for the anvil shaft.

Figure 5:
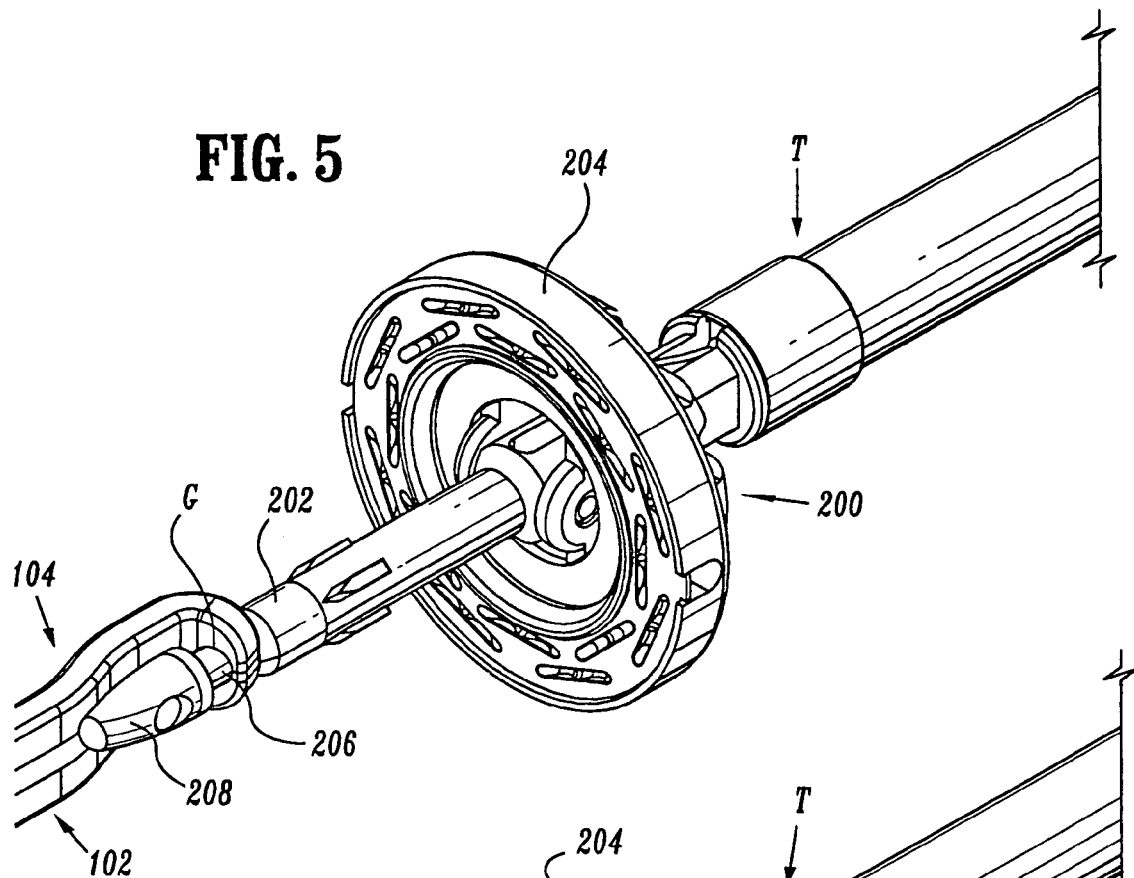
FIG. 5 is a perspective view of the jaw members shown in FIG. 2 illustrating the closed position of the jaw members around the proximal end portion of a shaft of an anvil assembly of a circular fastening apparatus.
Figure 6:
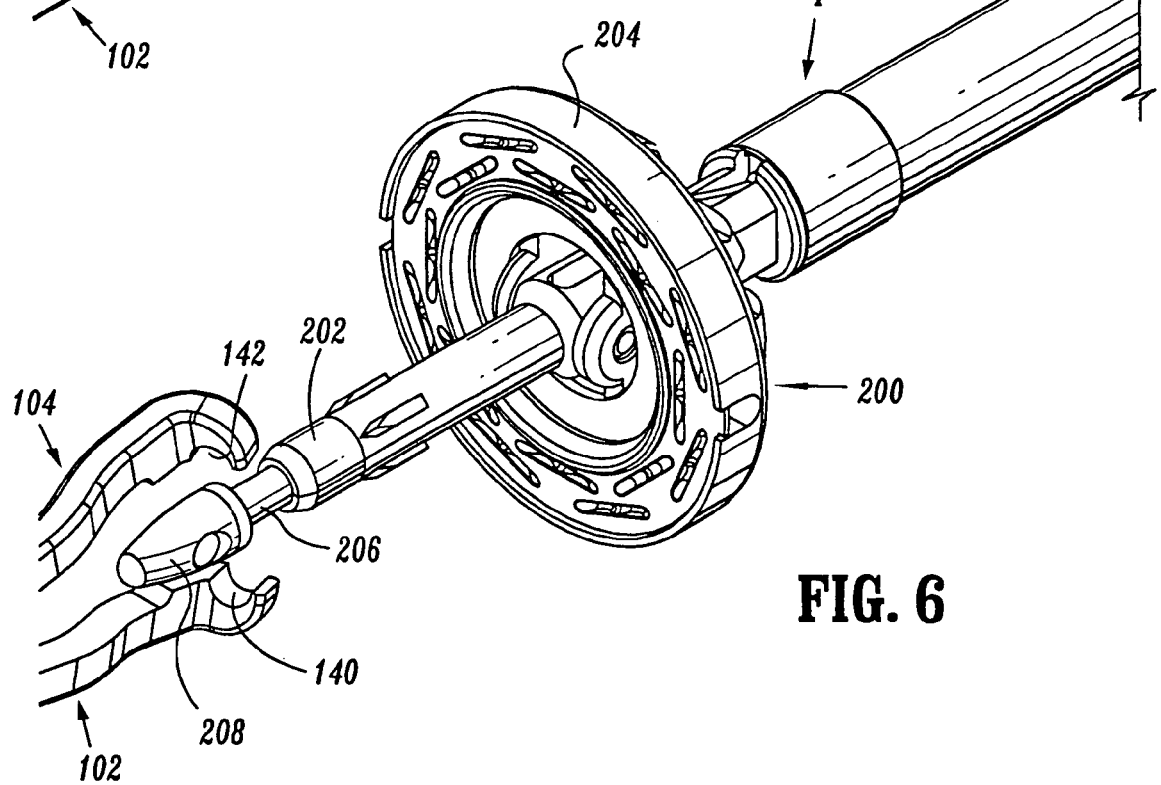
FIG. 6 is a perspective view of the jaw members shown in FIG. 2 illustrating the jaws in an open position about the proximal end portion of the shaft of the anvil assembly.

FIGS. 5 and 6 illustrate one example of the use of the invention in accordance with the present disclosure. As discussed above, typical instruments for performing a circular anastomosis of hollow organs include a detachable anvil assembly 200 having a shaft 202 and an attached or detachable anvil head 204, and/or a staple cartridge or cartridge assembly 212 (see FIG. 7) to provide circular stapling of the intestinal sections. It is to be understood that shaft 202 can be detached from an anvil, or can be a trocar shaft. In order to staple the intestinal sections of a patient to one another, anvil assembly 200 is previously inserted into an intestinal section (not shown) with the aid of an insertion instrument "T". The open end of the intestinal section is sutured or tied over the anvil head and about an attachment portion of the anvil shaft. 202. The cartridge assembly 212 (see FIG. 7) is previously inserted into the opposite intestinal section (not shown) whose open end is likewise disposed over and sutured about the distal end of the cartridge assembly.

It is envisioned that the sutured portions of the intestine are somewhat diagonally displaced from each other. Shaft 202 may have a recessed grasping portion 206, with a reduced cross section, near a distal end thereof, which, in accordance with the present invention, in FIG. 6, is to be engaged by recesses 140 and 142 of jaw members 102 and 104. In order to staple the two intestinal sections together, the operating surgeon grasps grasping portion 206 of shaft 202 with holding groove "G" of surgical jaw members 102 and 104 while manually or robotically holding or manipulating the frame or handle 14 of, or the endoscopic instrument 10 itself. The surgeon then pulls shaft 202 toward the cartridge assembly for insertion of tip 208 of shaft 202 into a guiding, receiving and engaging portion or the like (not shown) of the cartridge assembly.

Figure 7:
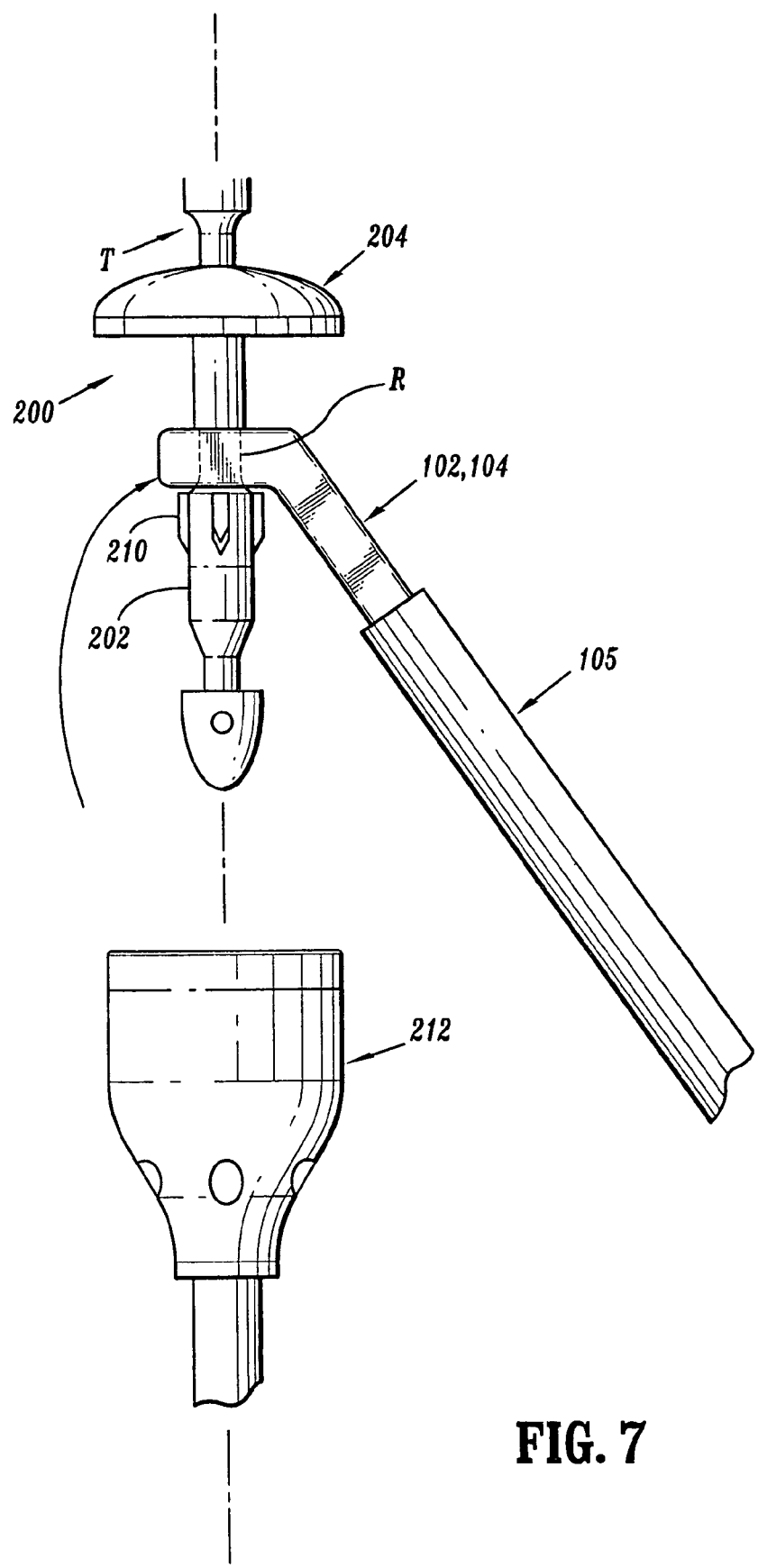
FIG. 7 is a side elevational view of the jaw members shown in FIG. 2 illustrating the closed position of the jaw members about an alternative shaft of an anvil assembly.

It is contemplated that jaw members 102 and 104, of the present invention, are adapted to engage and surround shaft 202 of anvil assembly 200 at various locations and orientations relative thereto. For example, as seen in FIG. 7, it is contemplated that jaw members 102 and 104 grasp shaft 202 at a location above or distally of splines 210, e.g., at recess "R" (dashed lines), which splines 210 are used to align shaft 202 with the staple firing mechanism 212 (i.e., cartridge assembly) with anvil assembly 200. In this manner, jaw members 102 and 104 do not interfere with the insertion of shaft 202 into the cartridge assembly 212. Thus, with this objective in mind, anvil shaft 202 preferably is adapted to be grasped at a location that is sufficiently removed, for example, more than a third, or half or more than half of the length of shaft 202 measured from the proximal end of the shaft.

It is further contemplated that the size and overall dimensions of endoscopic surgical instrument 10 are such that instrument 10 can be inserted into the patient via a 15 mm or 10 mm trocar. While an instrument which is insertable through a 15 mm or 10 mm trocar is disclosed, it is envisioned that the instrument can have any size and dimension.

The present invention provides substantial benefits to users compared to prior art devices. The jaws of the invention, facilitate grasping and manipulation of an object, such as shaft 202 of anvil assembly 200, toward and mounting it onto or into a targeted structure. However, it is appreciated that the surgical instrument of the invention may be used with any other elongated surgical instrument. The ease of manipulation provided by the design of the instrument is especially advantageous if there is limited operative space, e.g. if there are certain obstacles limiting the path of movement of the grasping instrument. More specifically, the jaws of the present invention enable the surgeon to approach and grasp the object, e.g., the shaft of or for the anvil, or a trocar, from a substantially longitudinally aligned direction with respect to the surgical instrument that has the jaws.

It will be understood that various modifications can be made to the embodiments of the present invention herein described without departing from the spirit of the invention herein. The invention in its broader aspects therefore is not limited to the specific embodiments herein shown and described but departures may be made therefrom within the scope of the accompanying claims without departing from the principles of the invention and without sacrificing its chief advantages.

What is claimed is:

1. A surgical grasping instrument for grasping an elongated implement which comprises:
   a frame dimensioned for engagement by the user;
   an elongated member connected to the frame and extending distally therefrom, the elongated member defining a longitudinal axis; and
   a pair of jaw members operatively connected to the elongated member, the jaw members being adapted for movement between an open position and a closed position, at least one of the jaw members having a facing surface with a recess therein and arranged about a central recess axis extending at an angle of less than about 30° relative to the longitudinal axis of the elongated member, wherein upon movement of the jaw members to the closed portion, the jaw members form a holding groove that can engage and firmly secure an elongated implement therein.

2. The grasping instrument according to claim 1, wherein each of the jaw members has the recess therein.

3. The grasping instrument according to claim 1, wherein the central recess axis is about 25° relative to the longitudinal axis of the elongated member.

4. The grasping instrument according to claim 1, wherein each jaw member includes a distal gripper portion, at least one distal gripper portion has the recess therethrough, and each distal gripper portion extends along an axis ranging from about 55° to about 75° relative to the longitudinal axis of the elongated member.

5. The grasping instrument according to claim 4, wherein the axis of each gripper portion is about 65° relative to the longitudinal axis.

6. An endoscopic surgical instrument for grasping a shaft of or for an anvil assembly of a circular stapling device, the surgical instrument comprising:
   a frame member;
   an elongate shaft, the elongate shaft having a proximal end operatively coupled to the frame member and a distal end, the elongate shaft defining a longitudinal axis;
   a pair or jaw members operatively coupled to the distal end of the elongate shaft, the pair of jaw members adapted to move between open and close positions, each of the pair of jaw members including a distal gripper portion having a recess therein, the recesses being juxtaposed to one another for grasping the shaft of or for the anvil therein such that when the jaw members are in the closed position, the recesses define a holding groove, the holding groove having an axis that is oriented at an angle which is less than about 30° relative to the longitudinal axis; and
   an actuation mechanism operatively coupled to the handle member extending through the shaft and being operatively coupled to a proximal end of the pair of jaw members in such a manner that the pair of jaw members open and close in response to an actuation of the frame member.

7. The endoscopic instrument according to claim 6, wherein the axis of the holding groove is oriented at an angle which is between about 15° to about 29° relative to the longitudinal axis.

8. The endoscopic instrument according to claim 6, wherein the axis of the holding groove is oriented at an angle which is about 25° relative to the longitudinal axis.

9. The endoscopic instrument according to claim 6, wherein the axis of the holding groove is parallel to the longitudinal axis.

10. The endoscopic instrument according to claim 6, wherein each jaw comprises:
    a base portion adapted to engage the distal end of the shaft; and
    a distal end portion having a longitudinal axis, and being located between the gripper portion and the base portion.

11. The endoscopic instrument according to claim 10, wherein the axis of the holding groove is oriented at an angle which is about 25° relative to the longitudinal axis of the distal end portion.

12. The endoscopic instrument according to claim 10, wherein the axis of the holding groove is parallel to the longitudinal axis of the distal end portion.

13. The endoscopic instrument according to claim 10, wherein each jaw member includes a base portion that has a diametric hole therethrough and about which the pair of jaws pivot.

14. The endoscopic instrument according to claim 10, wherein each base portion includes a cam slot formed proximally of the diametric holes, wherein the cam slots cooperate with one another to transform an axial movement of the actuation means into the opening and closing of the pair of jaw members.

15. The endoscopic instrument according to claim 6, wherein each jaw member includes a base portion and an adjacent intermediate body portion that includes a distal end portion which is parallel to the jaw axis and which is spaced a distance transversely from an axis defined by each base portion.

16. A surgical grasping instrument which comprises:

an elongated frame defining a longitudinal axis; and first and second jaw members coupled to the elongated frame, at least the first jaw member being adapted to move relative to the second jaw member between an initial position and a grasping position, each jaw member including:

a base portion defining a first axis;

an intermediate portion distal of the base portion and extending along a second axis traversing the first axis and in oblique relation to the longitudinal axis of the elongated frame; and a gripper portion distal of the intermediate portion and extending along a third axis traversing the second axis and in oblique relation to the longitudinal axis of the elongated frame, the gripper portion having inner surfaces defining a recess therein adapted for at least partially receiving a surgical implement to facilitate grasping of the instrument when in the grasping position of the jaw members, the recess arranged about a central recess axis, the central recess axis defining an angle less than about 30° relative to the longitudinal axis of the elongated frame; and a manually movable actuator for moving the first and second jaw members between the initial and grasping positions thereof.

17. The surgical grasping instrument according to claim 16 wherein the third axis defines an angle ranging from about 55° to about 75° relative to the longitudinal axis of the elongated frame.

18. The surgical grasping instrument according to claim 16 wherein the first of the base portion substantially parallel to the longitudinal axis of the elongated frame.

19. The surgical grasping instrument according to claim 16 wherein the central recess axis is in parallel relation to the longitudinal axis of the elongated frame.

* * * * *

UNITED STATES PATENT AND TRADEMARK OFFICE
CERTIFICATE OF CORRECTION

PATENT NO. : 7,144,409 B2 Page 1 of 1
APPLICATION NO. : 10/469774
DATED : December 5, 2006
INVENTOR(S) : Ernest Aranyi It is certified that error appears in the above-identified patent and that said Letters Patent is hereby corrected as shown below:

Column 10, Line 13: should read,

-- 18. The surgical grasping instrument according to claim 16 wherein the first axis of the base portion is substantially parallel to the longitudinal axis of the elongated frame. --

Signed and Sealed this

Sixth Day of November, 2007

JON W. DUDAS
*Director of the United States Patent and Trademark Office*